(12) United States Patent
Cordi et al.

(10) Patent No.: US 7,253,161 B2
(45) Date of Patent: Aug. 7, 2007

(54) BENZOTHIAZINE AND BENZOTHIADIAZINE DERIVATIVES METHOD FOR PREPARING SAME AND PHARMACEUTICAL COMPOSITIONS CONTAINING SAME

(75) Inventors: Alex Cordi, Suresnes (FR); Patrice Desos, Bois-Colombes (FR); Pierre Lestage, La Celle Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 18 days.

(21) Appl. No.: 10/498,948

(22) PCT Filed: Dec. 20, 2002

(86) PCT No.: PCT/FR02/04485

§ 371 (c)(1),
(2), (4) Date: Jun. 15, 2004

(87) PCT Pub. No.: WO03/053979

PCT Pub. Date: Jul. 3, 2003

(65) Prior Publication Data

US 2005/0124606 A1    Jun. 9, 2005

(30) Foreign Application Priority Data

Dec. 21, 2001 (FR) .................... 01 16621

(51) Int. Cl.
- *C07D 513/04* (2006.01)
- *A61K 31/542* (2006.01)
- *A61P 25/24* (2006.01)

(52) U.S. Cl. ........................ 514/222.8; 544/9; 514/215; 540/578

(58) Field of Classification Search .................... 544/9; 514/222.8, 215; 540/578
See application file for complete search history.

(56) References Cited

FOREIGN PATENT DOCUMENTS

| EP | 0692484 A | 1/1996 |
| EP | 1176148 A | 1/2002 |
| WO | WO 9942456 | 8/1999 |

OTHER PUBLICATIONS

Alt et al. Current Pharmaceutical Design, 2005, 11, 1511-1527.*
Black et al Psychopharmacology (2005) 179: 154-163.*
Daniel DeNoon, Schizophrenia Drug Face-Off: No Clear Winner, from the website http://www.webmd.com/content/Article/112/110297,htm?printing=true, downloaded on May 22, 2006.*
Maskell, et al., *Br. J. Pharmacol*, 2003, 140, 1313-1319.
Aracava, et al., *JPET*, 2005, 312, 1195-1250.
Advokat, et al., *Neurosci. Biobehav. Rev.*, 1992, 16, 13-24.
Danysz, et al., *Behav. Pharmacol.*, 1995, 6, 455-474.
Lynch, *Neurobiology of Learning and Memory*, 1998, 70, 82-100.
Robbins, et al., *TRENDS in Pharmacological Sciences*, 2006, 27 (3), 141-148.
Bliss, et al., *Nature*, 1993, 361, 31-39.
Ito, et al., *Journal of Physiology*, 1990, 424, 533-543.
Cumin, et al., *Psychopharmacology*, 1982, 78, 104-111.
Arai, et al., *Brain Res.*, 1994, 638, 343-346.
Miu, et al., *Neuropharmacol.*, 2001, 40, 976-983.
Staubli, et al., *Proc. Natl. Acad. Sci.*, 1994, 91, 777-781.
Lebrun, et al., *European Journal of Pharmacology*, 2000, 401, 205-212.
Rao, et al., *Neuroscience Letters*, 2001, 298, 183-186.
Thompson, et al., *Proc. Natl. Acad. Sci.*, 1995, 92, 7667-7671.
Buccafusco, et al., *Neuropharmacol.*, 2004, 46, 10-22.
Porrino, et al., *PLOS Biology*, 2005, 3 (9), 1639-1652.
Ingvar, et al., *Exp. Neurol.*, 1997, 146, 553-559.
Lynch, et al., *Exp. Neurol.*, 1997, 145, 89-92.
Baudry, *Neurobiology of Learning and Memory*, 2001, 76, 284-297.
Day, et al., *Nature*, 2003, 424, 205-209.
Lynch, *Current Opinion in Pharmacology*, 2006, 6, 82-88.
Lin, et al., *Brain Research*, 2002, 955, 164-173.

(Continued)

*Primary Examiner*—Kahsay Habte
(74) *Attorney, Agent, or Firm*—Hueschen and Sage

(57) ABSTRACT

Compounds of formula (I):

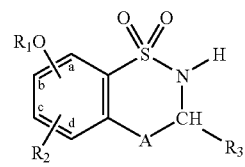

wherein:
$R_1$ represents aryl or heteroaryl,
$R_2$ represents hydrogen, halogen or hydroxy,
A represents $CR_4R_5$ or $NR_4$,
$R_3$ represents hydrogen, alkyl or cycloalkyl,
$R_4$ represents hydrogen or alkyl,
or
A represents nitrogen and, together with adjacent —$CHR_3$—, forms the ring

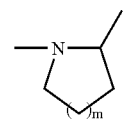

wherein m represents 1, 2 or 3,
$R_5$ represents hydrogen or halogen,
their isomers and also their addition salts.

Medicaments.

12 Claims, No Drawings

OTHER PUBLICATIONS

Desai, et al., *Neuropharmacology*, 1995, 34 (2), 141-147.
Lockhart, et al., *European Journal of Pharmacology*, 2000, 401, 145-153.
Jhee, et al., *J. Clin. Pharmacol.*, 2006, 46, 424-432.
Roger, et al., *Soc. Neurosci. Abstr.*, 2004, Abstract No. 219.11.
Dicou, et al., *Brain Research*, 2003, 970, 221-225.
Bahr, et al., *Exp. Neurol.*, 2002, 174, 37-47.
Murray, et al., *JPET*, 2003, 306, 752-762.
O'Neill, et al., *European Journal of Pharmacology*, 2004, 486, 163-174.
O'Neill, et al., *CNS Drug Rev.*, 2005, 11 (1), 77-96.
Bai, et al., *Neuropharmacology*, 2003, 44, 1013-1021.
Lauterborn, et al., *J. of Neuroscience*, 2000, 20 (1), 8-21.
Carrié, et al., *Soc. Neurosci. Abstr.*, 2005, Abstract No. 1018.4.
Lockhart, et al., *Soc. Neurosci. Abstr.*, 2004, Abstract No. 92.12.
Munoz, et al., *Soc. Neurosci. Abstr.*, 2004, Abstract No. 85.13.
Nibuya, et al., *J. of Neuroscience*, 1995, 15 (11), 7539-7547.
Dias, et al., *Neuropharmacology*, 2003, 45, 553-563.
Alt, et al., *Curr. Pharm. Des.*, 2005, 11 (12), 1511-1527.
Alt, et al., *Biochemical Pharmacology*, 2006, 71, 1273-1288.
Nakamura, et al., *Psychopharmacology*, 2001, 158, 205-212.
Li, et al., *Neuropharmacology*, 2001, 40, 1028-1033.
Knapp, et al., *European Journal of Pharmacology*, 2002, 440, 27-35.

\* cited by examiner

BENZOTHIAZINE AND BENZOTHIADIAZINE DERIVATIVES METHOD FOR PREPARING SAME AND PHARMACEUTICAL COMPOSITIONS CONTAINING SAME

The present invention relates to new benzothiazine and benzothiadiazine compounds, to a process for their preparation and to pharmaceutical compositions containing them.

It is now recognised that excitatory amino acids and, more especially, glutamate, play a crucial role in the physiological processes of neuronal plasticity and in the mechanisms underlying learning and memory. Pathophysiological studies have shown clearly that a deficiency in glutamatergic neurotransmission is closely associated with the development of Alzheimer's disease (Neuroscience and Biobehavioral reviews, 1992, 16, 13-24; Progress in Neurobiology, 1992, 39, 517-545).

Moreover, numerous studies over recent years have demonstrated the existence of excitatory amino acid receptor sub-types and their functional interactions (Molecular Neuropharmacology, 1992, 2, 15-31).

Among those receptors, the AMPA ("α-amino-3-hydroxy-5-methyl-4-isoxazole-propionic acid") receptor appears to be the receptor most implicated in the phenomena of physiological neuronal excitability and especially in those phenomena implicated in the processes of memorisation. For example, learning has been shown to be associated with an increase in the binding of AMPA to its receptor in the hippocampus, one of the cerebral regions essential to mnemocognitive processes. Similarly, nootropic agents, such as aniracetam, have very recently been described as modulating positively the AMPA receptors of neuronal cells (Journal of Neurochemistry, 1992, 58, 1199-1204).

In the literature, compounds of benzamide structure have been described as having that same mechanism of action and as improving mnesic performance (Synapse, 1993, 15, 326-329). Compound BA 74, in particular, is the most active of those new pharmacological agents.

Finally, patent specification EP 692 484 describes a benzothiadiazine compound having a facilitatory action on AMPA flux and patent application WO 99/42456 describes, inter alia, a number of benzothiadiazine compounds as modulators of AMPA receptors.

In addition to being new, the benzothiazine and benzothiadiazine compounds forming the subject-matter of the present invention surprisingly exhibit pharmacological activities in respect of AMPA flux that are clearly superior to those of the compounds of similar structure described in the prior art. They are useful as AMPA modulators in the treatment or prevention of mnemocognitive disorders associated with age, with anxiety or depressive syndromes, with progressive neurogenerative diseases, with Alzheimer's disease, with Pick's disease, with Huntington's chorea, with schizophrenia, with sequelae of acute neurodegenerative diseases, with sequelae of ischaemia and with sequelae of epilepsy.

The present invention relates more specifically to compounds of formula (I):

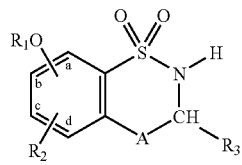

wherein:
$R_1$ represents an aryl or heteroaryl group,
$R_2$ represents a hydrogen atom, a halogen atom or a hydroxy group,
A represents a $CR_4R_5$ group or an $NR_4$ group,
$R_3$ represents a hydrogen atom, a linear or branched ($C_1$-$C_6$)alkyl group or a ($C_3$-$C_7$)cycloalkyl group,
$R_4$ represents a hydrogen atom or a linear or branched ($C_1$-$C_6$)alkyl group,
or
A represents a nitrogen atom and, together with the adjacent —$CHR_3$— group, forms the ring

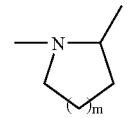

wherein m represents 1, 2 or 3,
$R_5$ represents a hydrogen atom or a halogen atom,
to their isomers and to their addition salts with a pharmaceutically acceptable acid or base, it being understood that:
"aryl group" is understood to mean an aromatic monocyclic group, or a bicyclic group in which at least one of the rings is aromatic, optionally substituted by one or more identical or different groups: halogen, linear or branched ($C_1$-$C_6$)alkyl (optionally substituted by one or more hydroxy groups), linear or branched ($C_1$-$C_6$) alkoxy, linear or branched ($C_1$-$C_6$)perhaloalkyl, linear or branched ($C_1$-$C_6$)alkoxycarbonyl, linear or branched ($C_1$-$C_6$)alkylthio, carboxy, linear or branched ($C_1$-$C_6$) acyl, linear or branched ($C_1$-$C_6$)perhaloalkoxy, hydroxy, cyano, nitro, amino (optionally substituted by one or more linear or branched ($C_1$-$C_6$)alkyl or linear or branched ($C_1$-$C_6$)acyl groups), aminocarbonyl (optionally substituted by one or more linear or branched ($C_1$-$C_6$)alkyl groups), aminosulphonyl (optionally substituted by one or more linear or branched ($C_1$-$C_6$)alkyl groups), mono- or di-(($C_1$-$C_6$)alkylsulphonyl)amino, mono- or di-(trifluoromethylsulphonyl)amino, $PO(OR_a)(OR_b)$ (wherein $R_a$, $R_b$, which may be identical or different, represent a hydrogen atom or a linear or branched ($C_1$-$C_6$)alkyl group), benzyloxy, or phenyl (optionally substituted by one or more identical or different groups: halogen, linear or branched ($C_1$-$C_6$) alkyl, linear or branched ($C_1$-$C_6$)perhaloalkyl, hydroxy or linear or branched ($C_1$-$C_6$)alkoxy),
"heteroaryl group" is understood to mean an aromatic monocyclic group, or a bicyclic group in which at least one of the rings is aromatic, containing one, two or three identical or different hetero atoms selected from nitrogen, oxygen and sulphur, optionally substituted by one or more identical or different groups: halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)alkoxycarbonyl, carboxy, linear or branched ($C_1$-$C_6$)acyl, linear or branched ($C_1$-$C_6$)perhaloalkoxy, hydroxy, cyano, nitro, amino (optionally substituted by one or more linear or branched ($C_1$-$C_6$)alkyl groups), aminosulphonyl (optionally substituted by one or more linear or branched ($C_1$-$C_6$)alkyl groups), or ($C_1$-$C_6$)alkylsulphonylamino.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

The $R_1O$— group is preferably in position b of the phenyl carrying it.

The preferred $R_1$ group is an aryl group, especially optionally substituted phenyl.

When the aryl group is a substituted phenyl group, the substituent is preferably in the meta position.

The preferred $R_2$ group is the hydrogen atom.

Preferred compounds of the invention are those wherein A represents a nitrogen atom and, together with the adjacent —$CHR_3$— group, forms the ring

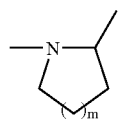

wherein m represents 1, 2 or 3 and preferably 1.

Preferred compounds of the invention are:
7-(3-methylphenoxy)-2,3,3a,4-tetrahydro-1H-pyrrolo[2,1-c][1,2,4]benzothiadiazine 5,5-dioxide,
3-[(5,5-dioxido-2,3,3a,4-tetrahydro-1H-pyrrolo[2,1-c][1,2,4]benzothiadiazin-7-yl)oxy]benzoic acid,
3-(5,5-dioxido-2,3,3a,4-tetrahydro-1H-pyrrolo[2,1-c][1,2,4]benzothiazin-7-yl)oxy]aniline,
N-[3-(5,5-dioxido-2,3,3a,4-tetrahydro-1H-pyrrido[2,1-c][1,2,4]benzothiazin-7-yl)oxy]phenyl]-methanesulphonamide,
ethyl hydrogen 3-[(5,5-dioxido-2,3,3a,4-tetrahydro-1H-pyrrolo[2,1-c][1,2,4]benzothiadiazin-7-yl)oxy]phenylphosphonate, and their isomers.

The invention relates also to a process for the preparation of compounds of formula (I).

The process for the preparation of compounds of formula (I) wherein A represents an $NR_4$ group or A represents a nitrogen atom and, together with the adjacent $CHR_3$ group, forms the ring

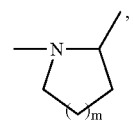

wherein m represents 1, 2 or 3, is characterised in that there is used as starting material a compound of formula (II):

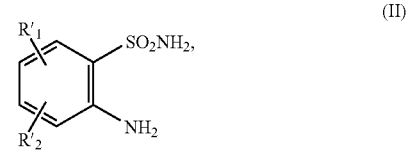

wherein:
$R'_1$ represents a linear or branched ($C_1$-$C_6$)alkoxy group,
$R'_2$ represents a hydrogen atom, a halogen atom or a linear or branched ($C_1$-$C_6$)alkoxy group, which is:
(a) either reacted with the acid chloride of formula (III) in the presence of a base, in a tetrahydrofuran or acetonitrile medium:

wherein m is as defined for formula (I),
to yield the compound of formula (IV):

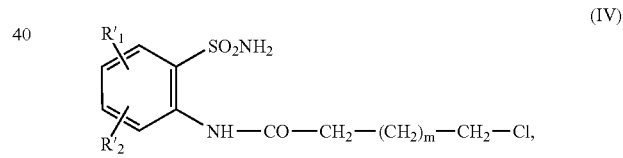

wherein $R'_1$ and $R'_2$ are as defined hereinbefore, which is then cyclised in basic medium to yield the compound of formula (V):

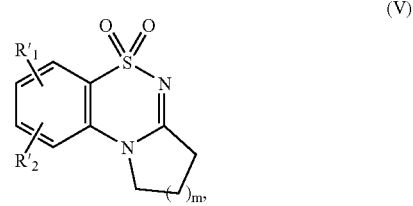

wherein $R'_1$, $R'_2$ and m are as defined hereinbefore, which is subjected to reduction, in alcoholic or dimethylformamide medium, in the presence of sodium borohydride, to yield the compound of formula (VI):

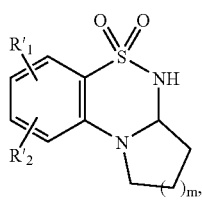

wherein R'$_1$, R'$_2$ and m are as defined hereinbefore,
which is subjected to the action of boron tribromide
to yield the compound of formula (VII):

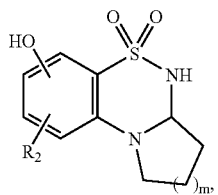

wherein R$_2$ and m are as defined hereinbefore,
(b) or cyclised
in the presence of an amidine of formula (VIII):

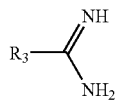

wherein:
R$_3$ is as defined for formula (I),
to yield the compound of formula (IX):

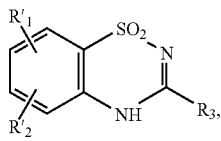

wherein R'$_1$, R'$_2$ and R'$_3$ are as defined hereinbefore,
which is:
either reduced with a metallic hydride
to yield the compound of formula (X):

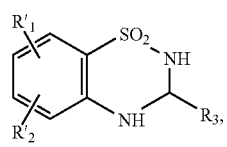

wherein R'$_1$, R'$_2$, and R'$_3$ are as defined hereinbefore,
or alkylated by the action of a strong base in the presence
of an alkylating agent R'$_4$X wherein R'$_4$ represents a
linear or branched (C$_1$-C$_6$)alkyl group and X represents
a halogen atom, and then reduced
to yield the compound of formula (XI):

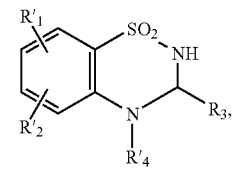

wherein R'$_1$, R'$_2$, R$_3$ and R'$_4$ are as defined hereinbefore, or
in the presence of an aldehyde of formula (XII):

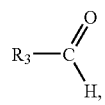

wherein R$_3$ is as defined for formula (I),
to yield the compound of formula (X) described above, the group R'$_1$ and the group R'$_2$, when it represents a linear
or branched (C$_1$-C$_6$)alkoxy group, of which compound of
formula (X) or (XI) are converted to hydroxy groups to yield
the compound of formula (XIII):

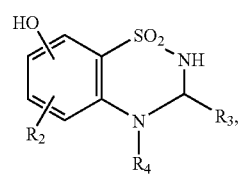

wherein R$_2$, R$_3$ and R$_4$ are as defined for formula (I),
which compound of formula (VII) or (XIII) is reacted with
a boronic acid compound of formula (XIV):

$$R_1B(OH)_2 \qquad (XIV),$$

wherein R$_1$ is as defined for formula (I),
to yield the compound of formula (I/a$_1$) or (I/a$_2$), particular
cases of the compounds of formula (I):

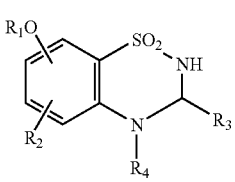

wherein R$_1$, R$_2$, R$_3$ and R$_4$ are as defined for formula (I),

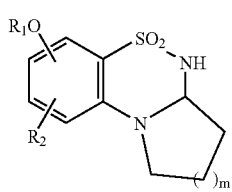
(I/a₂)

wherein R₁, R₂ and m are as defined for formula (I), which compounds of formula (I/a₁) or (I/a₂):

are subjected, if necessary, to conventional conversions in respect of the substituents of the group R₁, are, if necessary, purified according to a conventional purification technique, are optionally separated into the isomers according to a conventional separation technique and are converted, if desired, into their addition salts with a pharmaceutically acceptable acid or base.

The process for the preparation of compounds of formula (I) wherein A represents a $CR_4R_5$ group is characterised in that there is used as starting material a compound of formula (XV):

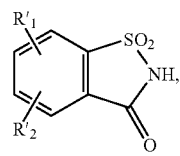
(XV)

wherein:

R'₁ represents a linear or branched ($C_1$-$C_6$)alkoxy group,

R'₂ represents a hydrogen atom, a halogen atom or a linear or branched ($C_1$-$C_6$)alkoxy group, which is subjected to the action of chloroacetone in the presence of dimethylformamide to yield the compound of formula (XVI):

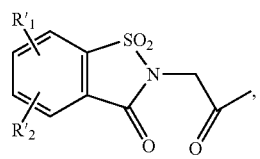
(XVI)

wherein R'₁ and R'₂ are as defined hereinbefore, which is subjected to rearrangement in basic medium to yield the compound of formula (XVII):

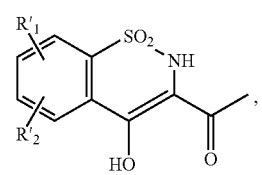
(XVII)

wherein R'₁ and R'₂ are as defined hereinbefore, which is deacetylated by heating at reflux in benzene medium in the presence of an excess of ethylene glycol and a catalytic amount of p-toluenesulphonic acid to yield the compound of formula (XVIII):

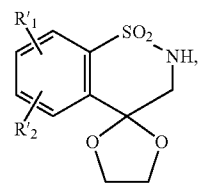
(XVIII)

wherein R'₁ and R'₂ are as defined hereinbefore, which is subjected to hydrolysis in acid medium to yield the compound of formula (XIXa):

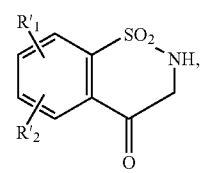
(XIXa)

wherein R'₁ and R'₂ are as defined hereinbefore, of which, optionally, according to the nature of the group R₃ it is desired to obtain, the nitrogen atom is protected by a protecting group, and which then, after treatment with a strong base, is treated with a compound of formula R'₃—P, wherein R'₃ represents a linear or branched ($C_1$-$C_6$)alkyl group or a ($C_3$-$C_7$)cycloalkyl group and P represents a leaving group, to yield, after deprotection of the nitrogen atom, the compound of formula (XIX'a):

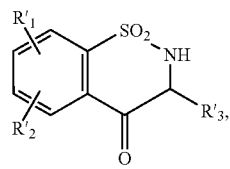
(XIX'a)

wherein R'$_1$, R'$_2$ and R'$_3$ are as defined hereinbefore, which compound of formula (XIXa) or (XIX'a), represented by formula (XIX):

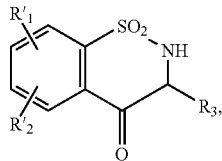
(XIX)

wherein R'$_1$ and R'$_2$ have the same meaning and R$_3$ is as defined for formula (I), is:

either subjected to catalytic reduction to yield the compound of formula (XX):

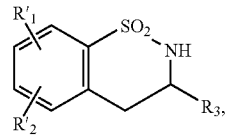
(XX)

wherein R'$_1$ and R'$_2$ are as defined hereinbefore,
or converted in alcohol by the action of a hydride the hydroxy group of which is converted to a halogen atom by the action of an appropriate reagent, to yield the compound of formula (XXI):

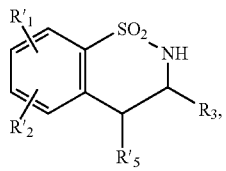
(XXI)

wherein R'$_1$ and R'$_2$ are as defined hereinbefore, R'$_5$ represents a halogen atom,
or subjected to the action of an organomagnesium compound R'$_4$ MgBr wherein R'$_4$ represents a linear or branched (C$_1$-C$_6$)alkyl group, to yield the compound of formula (XIXb):

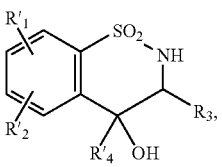
(XIXb)

wherein R'$_1$, R'$_2$ and R'$_4$ are as defined hereinbefore, which compound of formula (XIXb):
is either subjected to catalytic reduction to yield the compound of formula (XXII):

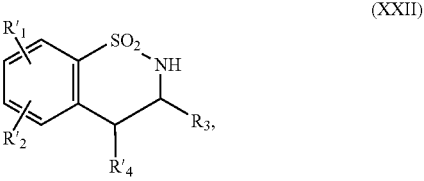
(XXII)

wherein R'$_1$, R'$_2$ and R'$_4$ are as defined hereinbefore,
or the hydroxy group of which is converted to a halogen atom by the action of an appropriate reagent,
to yield the compound of formula (XXIII):

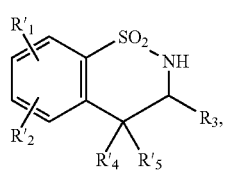
(XXIII)

wherein R'$_1$, R'$_2$ and R'$_4$ are as defined hereinbefore and R'$_5$ represents a halogen atom, the group R'$_1$ and the group R'$_2$, when it represents a linear or branched (C$_1$-C$_6$)alkoxy group, of which compounds of formulae (XX) to (XXIII) are converted to hydroxy groups to yield the compound of formula (XXIV):

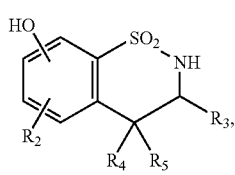
(XXIV)

wherein R$_2$, R$_4$ and R$_5$ are as defined for formula (I), which compound of formula (XXIV)

is reacted with a boronic acid compound of formula (XIV):

$$R_1B(OH)_2 \quad (XIV),$$

wherein R$_1$ is as defined for formula (I), to yield the compound of formula (I/b), a particular case of the compounds of formula (I):

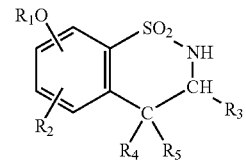
(I/b)

wherein R$_1$, R$_2$, R$_3$, R$_4$, R$_5$ are as defined for formula (I), which compound of formula (I/b) is subjected, if necessary, to conventional conversions in respect of the substituents of the group R$_1$, is purified, if necessary, according to a conventional purification technique, is optionally separated into the isomers according to a conventional separation technique and is converted, if desired, into addition salts with a pharmaceutically acceptable acid or base.

The invention extends also to pharmaceutical compositions comprising as active ingredient a compound of formula (I) with one or more appropriate inert, non-toxic excipients. Among the pharmaceutical compositions according to the invention there may be mentioned more especially those which are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, etc. . . .

The dosage used can be adapted according to the nature and the severity of the disorder, the administration route and the age and weight of the patient. The dosage ranges from 1 to 500 mg per day in one or more administrations.

The following Examples illustrate the invention but do not limit it in any way.

The starting materials used are known products or products prepared according to known procedures.

The structures of the compounds described in the Examples were determined according to customary spectrophotometric techniques (infra-red, NMR, mass spectrometry . . . ).

EXAMPLE 1

7-Phenoxy-2,3,3a,4-tetrahydro-1H-pyrrolo[2,1-c][1,2,4]benzothiadiazine 5,5-dioxide Step A: N-[2-(Aminosulphonyl)-4-methoxyphenyl]-4-chlorobutanamide 144 mmol of triethylamine and then, dropwise, a solution containing 135 mmol of 4-chlorobutanoic acid chloride in 30 ml of tetrahydrofuran (THF), are added to a solution containing 96.4 mmol of 2-amino-5-methoxybenzenesulphonamide in 200 ml of THF. After stirring overnight at ambient temperature, the THF is evaporated off and the residue is taken up in water. Following extraction with ethyl acetate, the organic phase is washed and dried. After evaporation, the expected product is obtained in the form of an oil.

Step B: 5,5-Dioxo-7-methoxy-2,3-dihydro-1H-pyrrolo[2,1-c][1,2,4]benzothiadiazine The product obtained in the above Step is stirred overnight at ambient temperature in 320 ml of an aqueous 1N sodium hydroxide solution. After the addition of 50 ml of ethyl acetate and stirring vigorously, the expected product, which precipitates, is filtered off, rinsed and dried.

Step C: 5,5-Dioxido-7-methoxy-2,3,3a,4-tetrahydro-1H-pyrrolo[2,1-c][1,2,4]benzothiadiazine 106.5 mmol of sodium borohydride are added to a suspension containing 35.5 mmol of the product obtained in the above Step in 40 ml of dimethylformamide (DMF). After stirring overnight at ambient temperature, the reaction mixture is cooled and then 150 ml of an iced solution of 1N hydrochloric acid are added to the above mixture. The expected product precipitates and is filtered off.

Melting point: 193-198° C.

Step D: 5,5-Dioxido-2,3,3a,4-tetrahydro-1H-pyrrolo[2,1-c][1,2,4]benzothiadiazin-7-ol 79.3 mmol of boron tribromide are added dropwise to a suspension containing 26.7 mmol of the product obtained in the above Step in 350 ml of dichloromethane maintained at −60° C. under nitrogen. The temperature is maintained for one hour and then the whole returns to ambient temperature and is stirred overnight. After cooling the reaction mixture in an ice bath, 100 ml of water are added and the biphasic system formed is stirred vigorously. The suspension so formed is filtered. The white solid obtained is washed with water, with ether, and dried, yielding the expected product.

Melting point: 237-242° C.

Step E: 7-Phenoxy-2,3,3a,4-tetrahydro-1H-pyrrolo[2,1-c][1,2,4]benzothiadiazine 5,5-dioxide A suspension containing 0.832 mmol of the compound obtained in the above Step, 1.66 mmol of phenylboronic acid, 1.25 mmol of copper acetate, 2.5 mmol of pyridine and 100 mg of molecular sieve is stirred for 5 hours in 20 ml of methylene chloride ($CH_2Cl_2$). After the addition of 20 ml of $CH_2Cl_2$, the suspension is filtered. After evaporation of the filtrate, the residue is purified on a silica column, using as eluant a methylene chloride/ethyl acetate (95/5) mixture, and yields the expected product.

Melting point: 239-243° C.

| | Elemental microanalysis: | | | |
|---|---|---|---|---|
| | C % | H % | N % | S % |
| calculated | 60.74 | 5.10 | 8.85 | 10.13 |
| found | 60.67 | 5.06 | 8.65 | 10.22 |

EXAMPLE 2

7-Phenoxy-2,3,3a,4-tetrahydro-1H-pyrrolo[2,1-c][1,2,4]benzothiadiazine 5,5-dioxide, α isomer

EXAMPLE 3

7-Phenoxy-2,3,3a,4-tetrahydro-1H-pyrrolo[2,1-c][1,2,4]benzothiadiazine 5,5-dioxide, β isomer The compounds of Examples 2 and 3 are obtained by separation of the isomers of Example 1 on a chiral column, Chiralcel OC®, using as eluting solvent a 1000/0.5 isopropanol/diethylamine mixture. After separation, each isomer is purified by chromatography on a silica column using as eluant a dichloromethane/ethyl acetate (20/10) mixture.

EXAMPLE 4

8-Phenoxy-2,3,3a,4-tetrahydro-1H-pyrrolo[2,1-c][1,2,4]benzothiadiazine 5,5-dioxide The compound of the following Example was obtained according to the procedure described in Example 1 using the appropriate starting material.

Melting point: 184-187° C.

| Elemental microanalysis: | | | |
|---|---|---|---|
| C % | H % | N % | S % |
| calculated 60.74 | 5.10 | 8.85 | 10.14 |
| found 60.24 | 5.04 | 8.69 | 10.09 |

The compounds of the following Examples were obtained according to the procedure described in Example 1 using the appropriate boronic acids in Step E.

EXAMPLE 5

4-[(5,5-Dioxido-2,3,3a,4-tetrahydro-1H-pyrrolo[2,1-c][1,2,4]benzothiadiazin-7-yl)oxy]benzonitrile Melting point: 242-245° C.

| Elemental microanalysis: | | | |
|---|---|---|---|
| C % | H % | N % | S % |
| calculated 59.81 | 4.43 | 12.31 | 9.39 |
| found 59.72 | 4.53 | 11.95 | 9.61 |

EXAMPLE 6

3-[(5,5-Dioxido-2,3,3a,4-tetrahydro-1H-pyrrolo[2,1-c][1,2,4]benzothiadiazin-7-yl)oxy]benzonitrile Melting point: 227-230° C.

| Elemental microanalysis: | | | |
|---|---|---|---|
| C % | H % | N % | S % |
| calculated 59.81 | 4.43 | 12.31 | 9.39 |
| found 59.87 | 4.50 | 11.79 | 9.12 |

EXAMPLE 7

7-(4-Methylphenoxy)-2,3,3a,4-tetrahydro-1H-pyrrolo[2,1-c][1,2,4]benzothiadiazine 5,5-dioxide Melting point: 222-226° C.

| Elemental microanalysis: | | | |
|---|---|---|---|
| C % | H % | N % | S % |
| calculated 61.80 | 5.49 | 8.48 | 9.70 |
| found 61.77 | 5.54 | 8.29 | 9.38 |

EXAMPLE 8

7-(3-Methylphenoxy)-2,3,3a,4-tetrahydro-1H-pyrrolo[2,1-c][1,2,4]benzothiadiazine 5,5-dioxide Melting point: 190-195° C.

| Elemental microanalysis: | | | |
|---|---|---|---|
| C % | H % | N % | S % |
| calculated 61.80 | 5.49 | 8.48 | 9.70 |
| found 62.16 | 5.55 | 8.22 | 9.56 |

EXAMPLE 9

7-(4-Methoxyphenoxy)-2,3,3a,4-tetrahydro-1H-pyrrolo[2,1-c][1,2,4]benzothiadiazine 5,5-dioxide Melting point: 188-191° C.

| Elemental microanalysis: | | | |
|---|---|---|---|
| C % | H % | N % | S % |
| calculated 58.94 | 5.24 | 8.09 | 9.26 |
| found 59.11 | 5.35 | 7.90 | 9.43 |

EXAMPLE 10

7-(3-Methoxyphenoxy)-2,3,3a,4-tetrahydro-1H-pyrrolo[2,1-c][1,2,4benzothiadiazine 5,5-dioxide Melting point: 152-155° C.

| Elemental microanalysis: | | | |
|---|---|---|---|
| C % | H % | N % | S % |
| calculated 58.94 | 5.24 | 8.09 | 9.26 |
| found 59.06 | 5.37 | 7.75 | 9.12 |

EXAMPLE 11

7-(3-Methoxyphenoxy)-2,3,3a,4-tetrahydro-1H-pyrrolo[2,1-c][1,2,4]benzothiadiazine 5,5-dioxide, α isomer

EXAMPLE 12

7-(3-Methoxyphenoxy)-2,3,3a,4-tetrahydro-1H-pyrrolo[2,1-c][1,2,4]benzothiadiazine 5,5-dioxide, β isomer The compounds of Examples 11 and 12 were obtained by separation of the compound of Example 10 on a chiral column under the same conditions as those described for Examples 2 and 3.

EXAMPLE 13

7-(2-Methoxyphenoxy)-2,3,3a,4-tetrahydro-1H-pyrrolo[2,1-c][1,2,4]benzothiadiazine 5,5-dioxide Melting point: 175-176° C.

Elemental microanalysis:

| | C % | H % | N % | S % |
|---|---|---|---|---|
| calculated | 58.94 | 5.24 | 8.09 | 9.26 |
| found | 58.91 | 5.34 | 7.93 | 9.26 |

EXAMPLE 14

7-(3-Trifluoromethylphenoxy)-2,3,3a,4-tetrahydro-1H-pyrrolo[2,1-c][1,2,4]benzothiadiazine 5,5-dioxide Melting point: 195-197° C.

Elemental microanalysis:

| | C % | H % | N % | S % |
|---|---|---|---|---|
| calculated | 53.12 | 3.93 | 7.29 | 8.34 |
| found | 53.31 | 4.05 | 7.20 | 8.22 |

The compounds of Examples 14a and 14b are obtained by separation of the enantiomers of Example 14 on a chiral column, Chiralcel OC®, under the same conditions as those described for Examples 2 and 3.

EXAMPLE 14a 7-(3-Trifluoromethylphenoxy)-2,3,3a,4-tetrahydro-1H-pyrrolo[2,1-c][1,2,4]benzothiadiazine 5,5-dioxide, α isomer Elemental microanalysis:

| | C % | H % | N % | S % |
|---|---|---|---|---|
| calculated | 53.12 | 3.93 | 7.29 | 8.34 |
| found | 53.05 | 4.29 | 7.21 | 8.08 |

EXAMPLE 14b 7-(3-Trifluoromethylphenoxy)-2,3,3a,4-tetrahydro-1H-pyrrolo[2,1-c][1,2,4]benzothiadiazine 5,5-dioxide, β isomer Elemental microanalysis:

| | C % | H % | N % | S % |
|---|---|---|---|---|
| calculated | 53.12 | 3.93 | 7.29 | 8.34 |
| found | 53.24 | 4.19 | 7.28 | 8.12 |

EXAMPLE 15

7-(3-Nitrophenoxy)-2,3,3a,4-tetrahydro-1H-pyrrolo[2,1-c][1,2,4]benzothiadiazine 5,5-dioxide Melting point: 201-204° C.

Elemental microanalysis:

| | C % | H % | N % | S % |
|---|---|---|---|---|
| calculated | 53.18 | 4.18 | 11.63 | 8.87 |
| found | 53.53 | 4.23 | 11.36 | 8.80 |

EXAMPLE 16

7-[3,5-Di(trifluoromethyl)phenoxy]-2,3,3a,4-tetrahydro-1H-pyrrolo[2,1-c][1,2,4]benzothiadiazine 5,5-dioxide Melting point: 201-203° C.

Elemental microanalysis:

| | C % | H % | N % | S % |
|---|---|---|---|---|
| calculated | 47.79 | 3.12 | 6.19 | 7.09 |
| found | 47.90 | 3.24 | 6.10 | 7.07 |

EXAMPLE 17

7-(3-Chlorophenoxy)-2,3,3a,4-tetrahydro-1H-pyrrolo[2,1-c][1,2,4]benzothiadiazine 5,5-dioxide Melting point: 194-198° C.

Elemental microanalysis:

| | C % | H % | N % | S % | Cl % |
|---|---|---|---|---|---|
| calculated | 54.78 | 4.31 | 7.99 | 9.14 | 10.11 |
| found | 54.92 | 4.36 | 7.91 | 9.15 | 10.95 |

EXAMPLE 18

7-(3-Ethoxyphenoxy)-2,3,3a,4-tetrahydro-1H-pyrrolo[2,1-c][1,2,4]benzothiadiazine 5,5-dioxide Melting point: 150° C.

Elemental microanalysis:

| | C % | H % | N % | S % |
|---|---|---|---|---|
| calculated | 59.98 | 5.59 | 7.77 | 8.90 |
| found | 60.11 | 5.64 | 7.56 | 8.61 |

EXAMPLE 19

7-(3-Trifluoromethoxyphenoxy)-2,3,3a,4-tetrahydro-1H-pyrrolo[2,1-c][1,2,4]benzothiadiazine 5,5-dioxide Melting point: 175° C.

Elemental microanalysis:

|  | C % | H % | N % | S % |
|---|---|---|---|---|
| calculated | 51.00 | 3.78 | 7.00 | 8.01 |
| found | 51.10 | 3.82 | 6.93 | 8.10 |

EXAMPLE 20

7-(1-Naphthyloxy)-2,3,3a,4-tetrahydro-1H-pyrrolo[2,1-c][1,2,4]benzothiadiazine 5,5-dioxide Melting point: 227-229° C.

Elemental microanalysis:

|  | C % | H % | N % | S % |
|---|---|---|---|---|
| calculated | 65.56 | 4.95 | 7.64 | 8.75 |
| found | 65.29 | 5.11 | 7.37 | 8.42 |

EXAMPLE 21

7-(2-Naphthyloxy)-2,3,3a,4-tetrahydro-1H-pyrrolo[2,1-c][1,2,4]benzothiadiazine 5,5-dioxide Melting point: 234-236° C.

Elemental microanalysis:

|  | C % | H % | N % | S % |
|---|---|---|---|---|
| calculated | 65.56 | 4.95 | 7.64 | 8.75 |
| found | 65.31 | 4.95 | 7.44 | 8.66 |

EXAMPLE 22

7-(3-Benzyloxyphenoxy)-2,3,3a,4-tetrahydro-1H-pyrrolo[2,1-c][1,2,4]benzothiadiazine 5,5-dioxide Melting point: 179-182° C.

Elemental microanalysis:

|  | C % | H % | N % | S % |
|---|---|---|---|---|
| calculated | 65.38 | 5.25 | 6.63 | 7.59 |
| found | 65.55 | 5.24 | 6.52 | 7.25 |

EXAMPLE 23

4-[(5,5-Dioxido-2,3,3a,4-tetrahydro-1H-pyrrolo[2,1-c][1,2,4]benzothiadiazin-7-yl)oxy]phenyl The expected product is obtained starting from the compound described in Example 9. There is added to that, after dissolution in methylene chloride and cooling in an ice bath, a solution of boron tribromide (1M) in $CH_2Cl_2$. After returning to ambient temperature and stirring overnight, the mixture is cooled in an ice bath. Following the addition of water, extraction with $CH_2Cl_2$, drying and evaporation, the expected product is obtained after filtering off the residue and taking up in ether and filtering.

Melting point: 175-178° C.

Elemental microanalysis:

|  | C % | H % | N % | S % |
|---|---|---|---|---|
| calculated | 57.82 | 4.85 | 8.43 | 9.65 |
| found | 57.66 | 4.83 | 8.18 | 9.63 |

EXAMPLE 24

3-[(5,5-Dioxido-2,3,3a,4-tetrahydro-1H-pyrrolo[2,1-c][1,2,4]benzothiadiazin-7-yl)oxy]phenyl The expected product is obtained by hydrogenation under atmospheric pressure at ambient temperature, for 5 hours, of 100 mg of the product of Example 22 in the presence of 20 mg of palladium/C in 20 ml of ethanol and 10 μl of concentrated hydrochloric acid. Following filtration and evaporation, the residue is taken up in ether and yields the expected product after filtration.

Melting point: 205-208° C.

Elemental microanalysis:

|  | C % | H % | N % | S % |
|---|---|---|---|---|
| calculated | 57.82 | 4.85 | 8.43 | 9.65 |
| found | 57.80 | 4.89 | 8.27 | 9.31 |

EXAMPLE 25

{3-[(5,5-Dioxido-2,3,3a,4-tetrahydro-1H-pyrrolo[2,1-c][1,2,4]benzothiadiazin-7-yl)oxy]phenyl}ethanone Melting point: 170-172° C.

Elemental microanalysis:

|  | C % | H % | N % | S % |
|---|---|---|---|---|
| calculated | 60.32 | 5.06 | 7.82 | 8.95 |
| found | 60.52 | 5.24 | 7.71 | 8.91 |

EXAMPLE 26

Methyl 3-[(5,5-dioxido-2,3,3a,4-tetrahydro-1H-pyrrolo[2,1-c][1,2,4]benzothiadiazin-7-yl)oxy]benzoate Melting point: 223-227° C.

| Elemental microanalysis: | | | |
|---|---|---|---|
| C % | H % | N % | S % |
| calculated 57.74 | 4.85 | 7.48 | 8.56 |
| found 57.49 | 5.02 | 7.31 | 8.37 |

EXAMPLE 27

3-[(5,5-Dioxido-2,3,3a,4-tetrahydro-1H-pyrrolo[2,1-c][1,2,4]benzothiadiazin-7-yl)oxy]benzoic acid 300 mg of the product of Example 26 are suspended in 5 ml of 1N NaOH. After stirring at reflux for one hour and acidification with 1N hydrochloric acid, the expected product is obtained after filtration.
Melting point: 271-274° C.

| Elemental microanalysis: | | | |
|---|---|---|---|
| C % | H % | N % | S % |
| calculated 56.66 | 4.47 | 7.77 | 8.90 |
| found 56.58 | 4.68 | 7.70 | 8.84 |

EXAMPLE 28

4-Methyl-7-phenoxy-3,4-dihydro-2H-1,2,4-benzothiadiazine 1,1-dioxide

Step A: 7-Methoxy-4H-1,2,4-benzothiadiazine 1,1-dioxide

There is stirred for 1 night at 80° C. a suspension of 3.0 g of 2-amino-5-methoxybenzene-sulphonamide in the presence of 1.31 g of formamidine hydrochloride and 2.27 ml of triethylamine in 50 ml of toluene. The toluene is evaporated off in vacuo. The residue is taken up in water and the precipitate is filtered off.
Melting point: 253-257° C.

Step B: 7-Methoxy-4-methyl-4H-1,2,4-benzothiadiazine 1,1-dioxide 2.88 g of the product obtained in the above Step are added portion by portion to a suspension of 9 ml of DMF containing 570 mg of 60% NaH in mineral oil. The mixture is stirred for 30 min. until a black solution is obtained. 929 µl of iodomethane are then added dropwise thereto. Stirring is continued for 1 h and the reaction mixture is precipitated by adding water. The precipitate is filtered off and rinsed with water and then with ether to yield the expected product.
Melting point: 205-209° C.

Step C: 7-Methoxy-4-methyl-3,4-dihydro-2H-1,2,4-benzothiadiazine 1,1-dioxide 1.19 g of sodium borohydride is added to a suspension of 2.37 g of the product of the above Step in 40 ml of ethanol. The mixture gradually becomes homogeneous. After reaction for 1 h at ambient temperature, the mixture is cooled in an ice bath and neutralised by the addition of 1N HCl. The white precipitate is stirred for 15 min. and the title product is filtered off.
Melting point: 126-128° C.

Step D: 4-Methyl-3,4-dihydro-2H-1,2,4-benzothiadiazin-7-ol 1,1-dioxide 79.3 mmol of boron tribromide are added dropwise to a suspension containing 2 g of the product obtained in the above Step in 200 ml of dichloromethane maintained at −60° C. under nitrogen. The temperature is maintained for one hour and then the whole returns to ambient temperature and is stirred overnight. After cooling the reaction mixture in an ice bath, 100 ml of water are added and the biphasic system is stirred vigorously. The suspension so formed is filtered. The solid obtained is washed with water, with ether, and dried, yielding the expected product.
Melting point: 168-172° C.

Step E: 4-Methyl-7-phenoxy-3,4-dihydro-2H-1,2,4-benzothiadiazine 1,1-dioxide

The expected product is obtained according to the procedure described in Step E of Example 1, starting from the compound described in the above Step.
Melting point: 141-145° C.

| Elemental microanalysis: | | | |
|---|---|---|---|
| C % | H % | N % | S % |
| calculated 57.92 | 4.86 | 9.65 | 11.04 |
| found 57.97 | 4.95 | 9.45 | 11.36 |

The compounds of Examples 29 to 32 were obtained according to the procedure described for Example 28 using appropriate starting materials.

EXAMPLE 29

4-Ethyl-7-phenoxy-3,4-dihydro-2H-1,2,4-benzothiadiazine 1,1-dioxide

Melting point: 179-181° C.

| Elemental microanalysis: | | | |
|---|---|---|---|
| C % | H % | N % | S % |
| calculated 59.19 | 5.30 | 9.20 | 10.53 |
| found 59.00 | 5.31 | 9.07 | 10.53 |

EXAMPLE 30

4-Propyl-7-phenoxy-3,4-dihydro-2H-1,2,4-benzothiadiazine 1,1-dioxide

Melting point: 143-145° C.

EXAMPLE 31

3-[(4-Ethyl-1,1-dioxido-3,4-dihydro-2H-1,2,4-benzothiadiazin-7-yl)oxy]benzonitrile Melting point: 143-146° C.

| Elemental microanalysis: | | | | |
|---|---|---|---|---|
| | C % | H % | N % | S % |
| calculated | 60.36 | 5.70 | 8.80 | 10.07 |
| found | 60.75 | 5.74 | 8.62 | 10.15 |

EXAMPLE 32

4-Ethyl-7-(3-methoxyphenoxy)-3,4-dihydro-2H-1,2,4-benzothiadiazine 1,1-dioxide

Melting point: 91-93° C.

| Elemental microanalysis: | | | | |
|---|---|---|---|---|
| | C % | H % | N % | S % |
| calculated | 58.34 | 4.59 | 12.76 | 9.74 |
| found | 58.71 | 4.68 | 12.44 | 9.49 |

EXAMPLE 33

7-Phenoxy-3,4-dihydro-2H-1,2-benzothiazine 1,1-dioxide

Step A: 6-Methoxy-2-(2-oxopropyl)-1,2-benzisothiazol-3(2H)-one 1,1-dioxide 360 mg of 6-methoxy-1,1-dioxo-1,2-dihydro-benzo[d]isothiazol-3-one are added in small portions to a suspension of 72 mg of 60% NaH in mineral oil in 1.6 ml of anhydrous dimethylformamide. After stirring for 30 min. at ambient temperature, the reaction mixture becomes homogeneous and 162 μl of chloroacetone are added thereto. The reaction mixture is heated at 110° C. for 30 min. It is allowed to return to ambient temperature, and then the mixture is precipitated by addition of water. The precipitate is filtered off, rinsed several times with water, suction-filtered off and dried in vacuo.

Melting point: 185-191° C.

| Elemental microanalysis: | | | | |
|---|---|---|---|---|
| | C % | H % | N % | S % |
| calculated | 57.47 | 5.43 | 8.38 | 9.59 |
| found | 57.17 | 5.40 | 8.01 | 9.41 |

Step B: 2-Acetyl-7-methoxy-2H-1,2-benzothiazin-4-ol 1,1-dioxide

A solution of sodium ethanolate in ethanol is prepared by dissolving 1.08 g of sodium in 23 ml of ethanol at reflux. The temperature of the solution is brought to 40° C. and 6.30 g of the product of Step A are added thereto with stirring. The reaction mixture becomes thicker. 5 ml of ethanol are added to allow stirring to be carried out, and heating for an additional 10 min. is carried out at 50-55° C. The reaction mixture is then cooled in an ice bath and acidified with 3N HCl and the yellow precipitate formed is filtered off.

Melting point: 162-166° C.

Step C: 7-Methoxy-2,3-dihydro-4H-1,2-benzothiazine-4,4-ethylenedioxy 1,1-dioxide 5.35 g of the product obtained in the above Step, 200 mg of para-toluenesulphonic acid and 5.6 ml of ethylene glycol are stirred at reflux in 200 ml of benzene in a round-bottomed flask on which a Dean-Stark apparatus is mounted. After refluxing for 72 h, the benzene is evaporated off in vacuo. The residue is dissolved in ethyl acetate and the organic phase is washed with water and then with saturated NaCl. Drying, filtration and evaporation are carried out and an oil is obtained which is crystallised from an ethyl ether/isopropyl ether mixture.

Melting point: 100-110° C.

Step D: 7-Methoxy-2,3-dihydro-4H-1,2-benzothiazin-4-one 1,1-dioxide

A solution of 2.63 g of the product of the above Step in a mixture of 50 ml of methanol and 50 ml of 3N HCl is stirred at reflux for 15 min. The methanol is evaporated off in vacuo and the aqueous phase is extracted with ether. The organic phase is dried and treated with animal black. Following filtration and evaporation, the residue is taken up in isopropyl ether and the solid is filtered off.

Melting point: 124-127° C.

Step E: 7-Methoxy-3,4-dihydro-2H-1,2-benzothiazine 1,1-dioxide 1.77 g of the product of the above Step in 40 ml of acetic acid is hydrogenated under 5 bar at 70° C. in the presence of 1.75 g of 10% Pd/C. The mixture is allowed to return to ambient temperature and the catalyst is filtered off. The filtrate is evaporated to dryness and the residue is chromatographed on silica, using a 95/5 methylene chloride/ethyl acetate system as eluant, to yield the expected product.

Melting point: 144-145° C.

Step F: 3,4-Dihydro-2H-1,2-benzothiazin-7-ol 1,1-dioxide 14.1 ml of a 1M solution of BBr$_3$ in methylene chloride are added dropwise to a solution of 1 g of the product of the above Step in 45 ml of methylene chloride cooled to −35° C. The mixture is allowed to return to ambient temperature. After stirring for 3 h at ambient temperature, the reaction mixture is poured into water at 5° C. and extraction is carried out with ethyl acetate. The organic phases are combined, washed with saturated NaCl, dried, filtered and evaporated.

A solid is obtained which is taken up in a small amount of isopropyl ether. The title product is filtered off.

Melting point: 173-177° C.

Step G:
7-Phenoxy-3,4-dihydro-2H-1,2-benzothiazine 1,1-dioxide

Starting from the compound described in the above Step, the expected product is obtained according to the procedure described in Step E of Example 1.

Melting point: 129-132° C.

| Elemental microanalysis: | | | | |
|---|---|---|---|---|
| | C % | H % | N % | S % |
| calculated | 61.07 | 4.76 | 5.09 | 11.65 |
| found | 61.40 | 4.85 | 5.11 | 11.40 |

The compounds of Examples 34 to 38 were obtained according to the procedure described in Example 1, using the appropriate arylboronic acid in Step E.

EXAMPLE 34

7-(3-Methylsulphanylphenoxy)-2,3,3a,4-tetrahydro-1H-pyrrolo[2,1-c][1,2,4]benzothiadiazine 5,5-dioxide Melting point: 160° C.

| Elemental microanalysis: | | | | |
|---|---|---|---|---|
| | C % | H % | N % | S % |
| calculated | 56.33 | 5.01 | 7.73 | 17.69 |
| found | 56.33 | 4.93 | 7.77 | 17.83 |

EXAMPLE 35

7-(3-Ethylphenoxy)-2,3,3a,4-tetrahydro-1H-pyrrolo[2,1-c][1,2,4]benzothiadiazine 5,5-dioxide Melting point: 143-144° C.

| Elemental microanalysis: | | | | |
|---|---|---|---|---|
| | C % | H % | N % | S % |
| calculated | 62.77 | 5.85 | 8.13 | 9.31 |
| found | 62.69 | 5.88 | 8.1 | 9.26 |

EXAMPLE 36

7-(3-Isopropylphenoxy)-2,3,3a,4-tetrahydro-1H-pyrrolo[2,1-c][1,2,4]benzothiadiazine 5,5-dioxide Melting point: 171-172° C.

| Elemental microanalysis: | | | | |
|---|---|---|---|---|
| | C % | H % | N % | S % |
| calculated | 63.66 | 6.19 | 7.81 | 8.95 |
| found | 63.63 | 6.18 | 7.77 | 8.69 |

EXAMPLE 37

7-(3-Fluorophenoxy)-2,3,3a,4-tetrahydro-1H-pyrrolo[2,1-c][1,2,4]benzothiadiazine 5,5-dioxide Melting point: 201° C.

| Elemental microanalysis: | | | | |
|---|---|---|---|---|
| | C % | H % | N % | S % |
| calculated | 57.47 | 4.52 | 8.38 | 9.59 |
| found | 57.06 | 4.51 | 8.15 | 9.63 |

EXAMPLE 38

7-(3-Bromophenoxy)-2,3,3a,4-tetrahydro-1H-pyrrolo[2,1-c][1,2,4]benzothiadiazine 5,5-dioxide Melting point: 193-195° C.

| Elemental microanalysis: | | | | | |
|---|---|---|---|---|---|
| | C % | H % | N % | S % | Br % |
| calculated | 48.62 | 3.82 | 7.09 | 8.11 | 20.21 |
| found | 48.95 | 3.82 | 7.03 | 8.13 | 20.02 |

EXAMPLE 39

3-[(5,5-Dioxido-2,3,3a,4-tetrahydro-1H-pyrrolo[2,1-c][1,2,4]benzothiadiazin-7-yl)oxy]benzamide A solution of 0.71 mmol of oxalyl chloride diluted with 1 ml of $CH_2Cl_2$ is added dropwise to a suspension of 5 ml of $CH_2Cl_2$ and 10 μl of DMF containing 0.46 mmol of the acid obtained in Example 27. The whole is stirred for 1 h 30 at ambient temperature and evaporated to dryness. In parallel, a solution of 5 ml of $CH_2Cl_2$ is saturated with ammonia, and then the acid chloride obtained above dissolved in 3 ml of $CH_2Cl_2$ is added dropwise thereto. After stirring for 2 h at ambient temperature, the reaction mixture is diluted with $CH_2Cl_2$ and the organic phase is washed in succession with 1N HCl, water and saturated NaCl. After drying ($MgSO_4$) and removal of the solvent by evaporation, the residue is triturated in a mixture of isopropyl ether and ethyl ether. The white solid is filtered off to yield the expected product.

Melting point: 139-142° C.

| Elemental microanalysis: | | | |
| --- | --- | --- | --- |
| C % | H % | N % | S % |
| calculated 56.81 | 4.77 | 11.69 | 8.92 |
| found 56.39 | 4.88 | 11.22 | 8.65 |

EXAMPLE 40

3-[(5,5-Dioxido-2,3,3a,4-tetrahydro-1H-pyrrolo[2,1-c][1,2,4]benzothiadiazin-7-yl)oxy]-N,N-dimethylbenzamide This compound is obtained according to the protocol of Example 39, replacing the ammonia with dimethylamine in the presence of pyridine.

Melting point: 199-202° C.

| Elemental microanalysis: | | | |
| --- | --- | --- | --- |
| C % | H % | N % | S % |
| calculated 58.9 | 5.46 | 10.85 | 8.28 |
| found 58.97 | 5.54 | 10.66 | 7.86 |

EXAMPLE 41

3-[(5,5-Dioxido-2,3,3a,4-tetrahydro-1H-pyrrolo[2,1-c][1,2,4]benzothiadiazin-7-yl)oxy]-N-methylbenzamide This compound is obtained according to the protocol of Example 39, replacing the ammonia with methylamine in the presence of pyridine.

Melting point: 130-135° C.

| Elemental microanalysis: | | | |
| --- | --- | --- | --- |
| C % | H % | N % | S % |
| calculated 57.88 | 5.13 | 11.25 | 8.59 |
| found 58.08 | 5.45 | 10.56 | 8.26 |

EXAMPLE 42

3-(5,5-Dioxido-2,3,3a,4-tetrahydro-1H-pyrrolo[2,1-c][1,2,4]benzothiazin-7-yl)oxy]aniline The product of Example 15 (2.19 mmol) is dissolved in a mixture of 100 ml of ethyl acetate and 50 ml of ethanol; 100 mg of 10% palladium-on-carbon are added and hydrogenation at atmospheric pressure is carried out for 1 h. The catalyst is filtered off, the filtrated is evaporated to dryness and the residue is precipitated from ether to yield the expected product after filtration.

Melting point: 221-226° C.

| Elemental microanalysis: | | | |
| --- | --- | --- | --- |
| C % | H % | N % | S % |
| calculated 57.99 | 5.17 | 12.68 | 9.68 |
| found 57.90 | 5.28 | 12.44 | 9.59 |

EXAMPLE 43

N-{3-[(5,5-Dioxido-2,3,3a,4-tetrahydro-1H-pyrrolo[2,1-c][1,2,4]benzothiadiazin-7-yl)oxy]phenyl}-N-(methylsulphonyl)methanesulphonamide 0.90 mmol of triethylamine, a spatula tip of DMAP and then, dropwise, 0.90 mmol of methanesulphonic anhydride diluted with 8 ml of $CH_2Cl_2$, are added to a solution of 0.45 mmol of amine of Example 42 in 30 ml of $CH_2Cl_2$. After one night at ambient temperature, the reaction mixture is washed (1N HCl, saturated NaCl), dried ($MgSO_4$). Purification of the 2 products formed is carried out by chromatography on silica, eluting with a $CH_2Cl_2$ 100%→$CH_2Cl_2$/MeOH 95/5 gradient. The first product eluted corresponds to the dimethylsulphonylated title product. The second, mono-methylsulphonylated compound corresponds to the product described in the following Example.

Melting point: 214-215° C.

| Elemental microanalysis: | | | |
| --- | --- | --- | --- |
| C % | H % | N % | S % |
| calculated 44.34 | 4.34 | 8.62 | 19.73 |
| found 44.72 | 4.55 | 8.55 | 19.84 |

EXAMPLE 44

N-{3-[(5,5-dioxido-2,3,3a,4-tetrahydro-1H-pyrrido[2,1-e][1,2,4]-benzothiazin-7-yl)-oxy]phenyl}methanesulphonamide As indicated in the above Example, the title product corresponds to the second product isolated by chromatography under the conditions mentioned.

Melting point: 117-120° C.

| Elemental microanalysis: | | | |
| --- | --- | --- | --- |
| C % | H % | N % | S % |
| calculated 49.86 | 4.68 | 10.26 | 15.66 |
| found 50.13 | 4.77 | 10.06 | 15.34 |

EXAMPLE 45

N-{3-[(5,5-Dioxido-2,3,3a,4-tetrahydro-1H-pyrrolo[2,1-c][1,2,4]benzothiadiazin-7-yl)oxy]phenyl}ethanesulphonamide This compound is obtained according to the procedure of Example 43, using the appropriate chlorosulphonyl.

Melting point: 169° C.

| Elemental microanalysis: | | | |
|---|---|---|---|
| C % | H % | N % | S % |
| calculated 51.05 | 5.00 | 9.92 | 15.14 |
| found 50.9 | 4.97 | 9.87 | 15.00 |

EXAMPLE 46

N-{3-[(5,5-Dioxido-2,3,3a,4-tetrahydro-1H-pyrrolo[2,1-c][1,2,4]benzothiadiazin-7-yl)oxy]phenyl}propane-2-sulphonamide This compound is obtained according to the procedure of Example 43, using the appropriate chlorosulphonyl.
Melting point: 179° C.

| Elemental microanalysis: | | | |
|---|---|---|---|
| C % | H % | N % | S % |
| calculated 52.16 | 5.30 | 9.60 | 14.66 |
| found 51.88 | 5.33 | 9.87 | 14.71 |

EXAMPLE 47

N-{3-[(5,5-Dioxido-2,3,3a,4-tetrahydro-1H-pyrrolo[2,1-c][1,2,4]benzothiadiazin-7-yl)oxy]phenyl}benzenesulphonamide This compound is obtained according to the procedure of Example 43, using the appropriate chlorosulphonyl.
Melting point: 142-145° C.

| Elemental microanalysis: | | | |
|---|---|---|---|
| C % | H % | N % | S % |
| calculated 56.04 | 4.49 | 8.91 | 13.60 |
| found 56.33 | 4.62 | 8.60 | 13.67 |

EXAMPLE 48

N-{3-[(5,5-Dioxido-2,3,3a,4-tetrahydro-1H-pyrrolo[2,1-c][1,2,4]benzothiadiazin-7-yl)oxy]phenyl}acetamide This compound is obtained according to the procedure of Example 43, using acetic anhydride.
Melting point: 251-253° C.

| Elemental microanalysis: | | | |
|---|---|---|---|
| C % | H % | N % | S % |
| calculated 57.89 | 5.13 | 11.25 | 8.59 |
| found 58.16 | 5.18 | 11.09 | 8.48 |

EXAMPLE 49

3-[(5,5-Dioxido-2,3,3a,4-tetrahydro-1H-pyrrolo[2,1-c][1,2,4]benzothiadiazin-7-yl)oxy]benzenesulphonamide Step A: 3-[(5,5-Dioxido-2,3,3a,4-tetrahydro-1H-pyrrolo[2,1-c][1,2,4]benzothiadiazin-7-yl)oxy]benzenesulphonyl Chloride A solution of 2 ml of glacial acetic acid and 340 µl of water is saturated with $SO_2$ by bubbling with $SO_2$ gas for 15 min. In parallel, at 5° C. a solution of 1.51 mmol of the amine of Example 42 is prepared in a mixture of 1.3 ml of glacial acetic acid and 2.4 ml of concentrated HCl. A solution of 1.7 mmol of sodium nitrite dissolved beforehand in 1 ml of water is added dropwise to that solution, and the reaction mixture is stirred for 30 min. at 5° C. 0.6 mmol of $CuCl_2.2H_2O$ is added to the solution which has been saturated with $SO_2$ and the suspension obtained is cooled to 5° C. The diazonium solution prepared above is added dropwise to the latter. The mixture is stirred for 1 h at 5° C. and then for 1 h 30 while allowing to return to ambient temperature. The reaction mixture is poured onto ice and the precipitate is filtered off and rinsed with water. After drying, the expected product is obtained in the form of a beige powder.

Step B: 3-[(5,5-Dioxido-2,3,3a,4-tetrahydro-1H-pyrrolo[2,1-c][1,2,4]benzothiadiazin-7-yl)oxy]benzenesulphonamide 0.48 mmol of the product of the above Step A in a mixture of 10 ml of 28% ammonium hydroxide, 2 ml of water and 1 ml of acetone is stirred overnight at ambient temperature. A slow transition to solution is observed and, after one night, a turbid orange solution is obtained. The solution is poured into 1N HCl cooled beforehand in an ice bath. The resulting suspension is stirred for 10 min. and the crude product is recovered by filtration. Purification is carried out by chromatography on silica using a 90/10 $CH_2Cl_2$/acetone mixture as eluant.
Melting point: 197-200° C.

| Elemental microanalysis: | | | |
|---|---|---|---|
| C % | H % | N % | S % |
| calculated 48.6 | 4.33 | 10.63 | 16.22 |
| found 48.81 | 4.49 | 10.23 | 16.27 |

EXAMPLE 50

3-[(5,5-Dioxido-2,3,3a,4-tetrahydro-1H-pyrrolo[2,1-c][1,2,4]benzothiadiazin-7-yl)oxy]-N-propylbenzenesulphonamide This compound is obtained by reaction of the product of Step A of Example 49 with the appropriate amine.
Melting point: 86-91° C.

| Elemental microanalysis: | | | |
|---|---|---|---|
| C % | H % | N % | S % |
| calculated 52.16 | 5.30 | 9.60 | 14.66 |
| found 52.96 | 5.30 | 9.33 | 14.41 |

EXAMPLE 51

3-[(5,5-Dioxido-2,3,3a,4-tetrahydro-1H-pyrrolo[2,1-c][1,2,4]benzothiadiazin-7-yl)oxy]-N-isopropyl-benzenesulphonamide This compound is obtained by reaction of the product of Step A of Example 49 with, the appropriate amine.
Melting point: 151-155° C.

| Elemental microanalysis: | | | |
|---|---|---|---|
| C % | H % | N % | S % |
| calculated 52.16 | 5.30 | 9.60 | 14.66 |
| found 52.41 | 5.50 | 9.68 | 14.66 |

EXAMPLE 52

Diethyl 3-[(5,5-dioxido-2,3,3a,4-tetrahydro-1H-pyrrolo[2,1-c][1,2,4]benzothiadiazin-7-yl)oxy]phenylphosphonate A mixture of 5.40 mmol of bromo compound of Example 38, 16.2 mmol of diethyl phosphite, 16.2 mmol of triethylamine, 1.62 mmol of Pd[P(Ph)$_3$]$_4$, is stirred overnight at 110° C. in 4 ml of DMF under a current of nitrogen. The DMF is evaporated off, the residue is taken up in ethyl acetate, and the organic phase is washed with a solution of 1N NaOH, water, saturated NaCl. After drying and evaporation in vacuo, a meringue is obtained which is crystallised from ether to yield the expected product.
Melting point: 148-152° C.

| Elemental microanalysis: | | | |
|---|---|---|---|
| C % | H % | N % | S % |
| calculated 53.09 | 5.57 | 6.19 | 7.09 |
| found 53.08 | 5.64 | 6.10 | 6.95 |

EXAMPLE 53

Ethyl hydrogen 3-[(5,5-dioxido-2,3,3a,4-tetrahydro-1H-pyrrolo[2,1-c][1,2,4]benzothiadiazin-7-yl)oxy]phenylphosphonate 0.66 mmol of the product of Example 52 in 3 ml of 1N NaOH is stirred for 8 h at 70° C. The reaction solution is acidified with 1N HCl and the white precipitate is filtered off to yield the expected product.
Melting point: 177-182° C.

| Elemental microanalysis: | | | |
|---|---|---|---|
| C % | H % | N % | S % |
| calculated 50.94 | 4.99 | 6.60 | 7.56 |
| found 50.85 | 5.02 | 6.59 | 7.65 |

EXAMPLE 54

3-[(5,5-Dioxido-2,3,3a,4-tetrahydro-1H-pyrrolo[2,1-c][1,2,4]benzothiadiazin-7-yl)oxy]phenylphosphonic acid Acetonitrile (20 ml), 0.66 mmol of the product of Example 52 and 1.98 mmol of bromotrimethylsilane are stirred at reflux for 1 h. The solvent and the excess of reagent are evaporated off in vacuo and the residue is taken up in solution in 10 ml of methanol. After stirring for 30 min., the solution is evaporated to dryness and the residue is taken up in 1N HCl. A gum is obtained which is crystallised by adding a small amount of CH$_2$Cl$_2$. The expected product is recovered by filtration.
Melting point: 166-169° C.

| Elemental microanalysis: | | | |
|---|---|---|---|
| C % | H % | N % | S % |
| calculated 48.49 | 4.32 | 7.07 | 8.09 |
| found 48.34 | 4.29 | 7.00 | 8.06 |

EXAMPLE 55

7-(3-Methylphenoxy)-3,4-dihydro-2H-1,2-benzothiazine 1,1-dioxide

Prepared by coupling the product obtained in Step F of Example 33 and 3-methylphenyl-boronic acid according to the procedure described in Step E of Example 1.
Melting point: 116-118° C.

| Elemental microanalysis: | | | |
|---|---|---|---|
| C % | H % | N % | S % |
| calculated 62.26 | 5.23 | 4.84 | 11.08 |
| found 62.69 | 5.17 | 4.94 | 10.90 |

The compounds of Examples 56 to 61 were obtained according to the procedure described for Example 28 using ethyl iodide in Step B and the appropriate arylboronic acid in Step E.

EXAMPLE 56

4-Ethyl-7-[(3-methylsulphanyl)phenoxy]-3,4-dihydro-2H-[1,2,4]benzothiadiazine 1,1-dioxide Melting point: 127-130° C.

| Elemental microanalysis: | | | |
|---|---|---|---|
| C % | H % | N % | S % |
| calculated 54.83 | 5.18 | 7.99 | 18.30 |
| found 54.80 | 5.16 | 7.97 | 18.22 |

EXAMPLE 57

4-Ethyl-7-(3-methylphenoxy)-3,4-dihydro-2H-[1,2,4]benzothiadiazine 1,1-dioxide

Melting point: 72-75° C.

| Elemental microanalysis: | | | |
|---|---|---|---|
| C % | H % | N % | S % |
| calculated 60.36 | 5.70 | 8.80 | 10.07 |
| found 60.6 | 5.64 | 8.82 | 9.97 |

EXAMPLE 58

N-{3-[(4-Ethyl-1,1-dioxido-3,4-dihydro-2H-1,2,4-benzothiadiazin-7-yl)oxy]phenyl}methanesulphonamide Melting point: 165-168° C.

| Elemental microanalysis: | | | |
|---|---|---|---|
| C % | H % | N % | S % |
| calculated 48.35 | 4.82 | 10.57 | 16.13 |
| found 48.74 | 5.02 | 10.39 | 16.22 |

EXAMPLE 59

1-{3-[(4-Ethyl-1,1-dioxido-3,4-dihydro-2H-1,2,4-benzothiadiazin-7-yl)oxy]phenyl}ethanone Melting point: 164-166° C.

| Elemental microanalysis: | | | |
|---|---|---|---|
| C % | H % | N % | S % |
| calculated 58.94 | 5.24 | 8.09 | 9.26 |
| found 59.06 | 5.24 | 7.81 | 8.88 |

EXAMPLE 60

Ethyl-7-(3-thienyloxy)-3,4-dihydro-2H-benzo[1,2,4]thiadiazine 1,1-dioxide

Melting point: 152-154° C.

| Elemental microanalysis: | | | |
|---|---|---|---|
| C % | H % | N % | S % |
| calculated 50.30 | 4.55 | 9.03 | 20.66 |
| found 50.26 | 4.42 | 8.92 | 20.97 |

EXAMPLE 61

7-(3,4-Dimethylphenoxy)-4-ethyl-3,4-dihydro-2H-1,2,4-benzothiadiazine 1,1-dioxide Melting point: 109-111° C.

| Elemental microanalysis: | | | |
|---|---|---|---|
| C % | H % | N % | S % |
| calculated 61.42 | 6.06 | 8.43 | 9.65 |
| found 61.37 | 6.09 | 8.25 | 9.36 |

EXAMPLE 62

3-[(4-Ethyl-1,1-dioxido-3,4-dihydro-2H-1,2,4-benzothiadiazin-7-yl)oxy]aniline

This compound is obtained by reduction of the nitro product of Example 15 according to the procedure described in Example 42.

Melting point: 128-132° C.

| Elemental microanalysis: | | | |
|---|---|---|---|
| C % | H % | N % | S % |
| calculated 56.41 | 5.37 | 13.16 | 10.04 |
| found 56.84 | 5.53 | 12.89 | 10.17 |

EXAMPLE 63

N-{3-[(4-Ethyl-1,1-dioxido-3,4-dihydro-2H-1,2,4-benzothiadiazin-7-yl)oxy]phenyl}-1,1,1-trifluoromethanesulphonamide This compound is obtained by reaction of the amine of Example 62 with trifluoromethanesulphonic anhydride under the conditions described in Example 43.

Melting point: 136-138° C.

| Elemental microanalysis: | | | |
|---|---|---|---|
| C % | H % | N % | S % |
| calculated 42.57 | 3.57 | 9.31 | 14.21 |
| found 43.24 | 3.76 | 9.10 | 14.33 |

EXAMPLE 64

1-{3-[(4-Ethyl-1,1-dioxido-3,4-dihydro-2H-1,2,4-benzothiadiazin-7-yl)oxy]phenyl}ethanol To 0.8 ml of anhydrous ethanol there are added in small portions 0.42 mmol of NaBH$_4$ then 0.21 mmol of the product of Example 59. The solution is stirred for 20 min. at ambient temperature. The reaction mixture is cooled in an ice bath and acidified by the dropwise addition of 1N HCl. The reaction mixture is extracted with ethyl acetate and the organic phase is washed (water, saturated NaCl), dried (MgSO$_4$) and evaporated to yield the expected product.
Melting point: 60° C.

| Elemental microanalysis: | | | | |
|---|---|---|---|---|
| | C % | H % | N % | S % |
| calculated | 58.60 | 5.79 | 8.04 | 9.20 |
| found | 58.57 | 5.71 | 7.75 | 8.97 |

EXAMPLE 65

3-[(4-Ethyl-1,1-dioxido-3,4-dihydro-2H-1,2,4-benzothiadiazin-7-yl)oxy]benzoic acid This compound is obtained according to the procedure described in Example 27.
Melting point: 228-230° C.

| Elemental microanalysis: | | | | |
|---|---|---|---|---|
| | C % | H % | N % | S % |
| calculated | 55.16 | 4.63 | 8.04 | 9.20 |
| found | 54.89 | 4.69 | 7.89 | 9.32 |

EXAMPLE 66

3-[(4-Ethyl-1,1-dioxido-3,4-dihydro-2H-1,2,4-benzothiadiazin-7-yl)oxy]benzamide

This compound is obtained by amidation of the product of Example 65 according to the procedure of Example 39.
Melting point: 85-90° C.

| Elemental microanalysis: | | | | |
|---|---|---|---|---|
| | C % | H % | N % | S % |
| calculated | 55.32 | 4.93 | 12.10 | 9.23 |
| found | 55.21 | 5.13 | 11.52 | 8.85 |

EXAMPLE 67

3-[(4-Ethyl-1,1-dioxido-3,4-dihydro-2H-1,2,4-benzothiadiazin-7-yl)oxy]-N,N-dimethylbenzamide This compound is obtained by amidation of the product of Example 65 according to the procedure of Example 40.
Melting point: 65-70° C.

| Elemental microanalysis: | | | | |
|---|---|---|---|---|
| | C % | H % | N % | S % |
| calculated | 57.58 | 5.64 | 11.19 | 8.54 |
| found | 57.54 | 5.78 | 10.55 | 8.20 |

EXAMPLE 68

3-Phenoxy-6,6a,7,8,9,10-hexahydropyrido[2,1-c][1,2,4]benzothiadiazine 5,5-dioxide This compound is obtained according to the procedure described in Example 1 using 5-chloropropanoic acid chloride in Step A.
Melting point: 211-213° C.

| Elemental microanalysis: | | | | |
|---|---|---|---|---|
| | C % | H % | N % | S % |
| calculated | 61.80 | 5.49 | 8.48 | 9.70 |
| found | 61.61 | 5.45 | 8.35 | 9.79 |

Pharmacological Study of the Products of the Invention

Study of the Excitatory Fluxes Induced by AMPA in *Xenopus* Oocytes a—Method:

mRNAs are prepared from cerebral cortex of male Wistar rat by the guanidinium thiocyanate/phenyl/chloroform method. The poly-(A$^+$) mRNAs are isolated by chromatography on oligo-dT cellulose and injected in an amount of 50 ng per oocyte. The oocytes are left to incubate for 2 to 3 days at 18° C. to allow expression of the receptors and are then stored at from 8 to 10° C.

Electrophysiological recording is carried out in a Plexiglass® chamber at from 20 to 24° C. in OR2 medium (J. Exp. Zool., 1973, 184, 321-334) by the 2-electrode "voltage-clamp" method, a 3rd electrode being placed in the bath to serve as reference.

All the compounds are administered via the incubation medium and the electric current is measured at the end of the period of administration. AMPA is used at a concentration of 10 μM. For each compound studied, the concentration that doubles (EC2×) or quintuples (EC5×) the intensity of the current induced by AMPA alone (5 to 50 nA) is determined.

b—Results:

The compounds of the invention potentiate very substantially the excitatory effects of AMPA and their activity is very clearly superior to that of the reference compounds. The compound of Example 3, especially, has an EC2× of 0.8 μM and a EC5× of 3.6 μM. As for the compound of Example 29, it has an EC2× of 1.4 μM and an EC5× of 4.5 μM.

| PHARMACEUTICAL COMPOSITION Formulation for the preparation of 1000 tablets each comprising a dose of 100 mg | |
|---|---|
| compound of Example 1 | 100 g |
| hydroxypropyl cellulose | 2 g |
| wheat starch | 10 g |
| lactose | 100 g |
| magnesium stearate | 3 g |
| talc | 3 g |

What is claimed is:

1. A compound selected from those of formula (I):

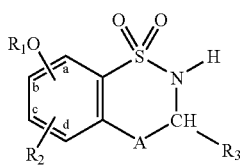

wherein:
- $R_1$ represents aryl or heteroaryl,
- $R_2$ represents hydrogen, halogen or hydroxy,
- A represents $NR_4$, and $R_3$ and $R_4$, together with the carbon and nitrogen atoms to which they are attached, form a ring

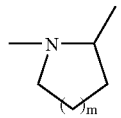

wherein m represents 1, 2 or 3,
its isomers and addition salts thereof with a pharmaceutically acceptable acid or base,
it being understood that:
"aryl" may be an aromatic monocyclic group or a bicyclic group in which at least one of the rings is aromatic, each of those groups being optionally substituted by one or more identical or different halogen, linear or branched ($C_1$-$C_6$)alkyl (optionally substituted by one or more hydroxy groups), linear or branched ($C_1$-$C_6$)alkoxy, linear or branched ($C_1$-$C_6$)perhaloalkyl, linear or branched ($C_1$-$C_6$)alkoxycarbonyl, linear or branched ($C_1$-$C_6$)alkylthio, carboxy, linear or branched ($C_1$-$C_6$)acyl, linear or branched ($C_1$-$C_6$)perhaloalkoxy, hydroxy, cyano, nitro, amino (optionally substituted by one or more linear or branched ($C_1$-$C_6$)alkyl or linear or branched ($C_1$-$C_6$)acyl), aminocarbonyl (optionally substituted by one or more linear or branched ($C_1$-$C_6$)alkyl), aminosulphonyl (optionally substituted by one or more linear or branched ($C_1$-$C_6$)alkyl), mono- or di-(($C_1$-$C_6$)alkylsulphonyl)amino, mono- or di-(trifluoromethylsulphonyl)amino, $PO(OR_a)(OR_b)$ (wherein $R_a$, $R_b$, which may be identical or different, represent hydrogen or linear or branched ($C_1$-$C_6$)alkyl), benzyloxy, or phenyl (optionally substituted by one or more identical or different halogen, linear or branched ($C_1$-$C_6$)alkyl, linear or branched ($C_1$-$C_6$)perhaloalkyl, hydroxy or linear or branched ($C_1$-$C_6$)alkoxy), "heteroaryl" may be an aromatic monocyclic group, or a bicyclic group in which at least one of the rings is aromatic, containing one, two or three identical or different hetero atoms selected from nitrogen, oxygen and sulphur, each of those groups being optionally substituted by one or more identical or different halogen, linear or branched ($C_1$-$C_6$)alkyl, linear or branched ($C_1$-$C_6$)alkoxy, linear or branched ($C_1$-$C_6$)perhaloalkyl, linear or branched ($C_1$-$C_6$)alkoxycarbonyl, carboxy, linear or branched ($C_1$-$C_6$)acyl, linear or branched ($C_1$-$C_6$)perhaloalkoxy, hydroxy, cyano, nitro, amino (optionally substituted by one or more linear or branched ($C_1$-$C_6$)alkyl), aminosulphonyl (optionally substituted by one or more linear or branched ($C_1$-$C_6$)alkyl), or ($C_1$-$C_6$)-alkylsulphonylamino.

2. A compound of claim 1 wherein $R_2$ represents hydrogen.

3. A compound of claim 1 wherein the $OR_1$ group is in the b position of the phenyl ring carrying it.

4. A compound of claims 1 wherein $R_1$ represents optionally substituted phenyl.

5. A compound of claim 1 wherein m represents 1.

6. A compound of claim 1 which is 7-(3-methylphenoxy)-2,3,3a,4-tetrahydro-1H-pyrrolo[2,1-c][1,2,4]benzothiadiazine 5,5-dioxide, and its isomers.

7. A compound of claim 1 which is 3-[(5,5-dioxido-2,3,3a,4-tetrahydro-1H-pyrrolo[2,1-c][1,2,4]benzothiadiazin-7-yl)oxy]benzoic acid, and its isomers.

8. A compound of claim 1 which is 3-(5,5-dioxido-2,3,3a,4-tetrahydro-1H-pyrrolo[2,1-c][1,2,4]benzothiazin-7-yl)oxy]aniline, and its isomers.

9. A compound of claim 1 which is N-[3-(5,5-dioxido-2,3,3a,4-tetrahydro-1H-pyrrolo[2,1-c][1,2,4]benzothiazin-7-yl)oxy]phenyl)methanesulphonamide, and its isomers.

10. A compound of claim 1 which is ethyl hydrogen 3-[(5,5-dioxido-2,3,3a,4-tetrahydro-1H-pyrrolo[2,1-c][1,2,4]benzothiadiazin-7-yl)oxy]phenyl-phosphonate, and its isomers.

11. A pharmaceutical composition comprising as active principle an effective amount of a compound of claim 1, together with one or more pharmaceutically acceptable excipients or vehicles.

12. A method for treating a living animal body, including a human, afflicted with a condition selected from anxiety and depression, comprising the step of administering to the living animal body, including a human, an amount of a compound of claim 1 which is effective for alleviation of the condition.

* * * * *